(12) United States Patent
Liu

(10) Patent No.: US 9,578,899 B2
(45) Date of Patent: Feb. 28, 2017

(54) ELECTRONIC CIGAR

(71) Applicant: Qiuming Liu, Guangdong (CN)

(72) Inventor: Qiuming Liu, Guangdong (CN)

(73) Assignee: HUIZHOU KIMREE TECHNOLOGY CO., LTD. SHENZHEN BRANCH, Shenzhen (CN)

( * ) Notice: Subject to any disclaimer, the term of this patent is extended or adjusted under 35 U.S.C. 154(b) by 711 days.

(21) Appl. No.: 13/959,421

(22) Filed: Aug. 5, 2013

(65) Prior Publication Data

US 2014/0352707 A1 Dec. 4, 2014

Related U.S. Application Data

(63) Continuation of application No. PCT/CN2013/076608, filed on May 31, 2013.

(51) Int. Cl.
| | |
|---|---|
| A24F 47/00 | (2006.01) |
| A24F 7/02 | (2006.01) |
| A24F 13/02 | (2006.01) |
| A61M 11/04 | (2006.01) |
| A61M 15/00 | (2006.01) |
| A61M 16/06 | (2006.01) |

(52) U.S. Cl.
CPC ............ *A24F 47/008* (2013.01); *A61J 1/1418* (2015.05); *A61J 1/1481* (2015.05); *A24F 47/002* (2013.01); *A61J 1/1425* (2015.05); *A61M 11/044* (2014.02); *A61M 15/0021* (2014.02); *A61M 16/06* (2013.01)

(58) Field of Classification Search
CPC ...... A24F 47/008; A24F 47/00; A24F 47/002; A24F 1/00; A24F 7/02; A24F 1/02; A61M 15/06; A61M 16/06; A61M 11/044; A61M 15/0021; A61J 1/1418; A61J 1/1425; A61J 1/1481
USPC .................................................. 131/225, 329
See application file for complete search history.

(56) References Cited

U.S. PATENT DOCUMENTS

| | | | | |
|---|---|---|---|---|
| 192,123 | A * | 6/1877 | May ........................... | A24F 7/00 131/225 |
| 4,429,703 | A * | 2/1984 | Haber .................... | A24F 47/002 131/273 |
| 4,945,931 | A * | 8/1990 | Gori ....................... | A24F 47/008 131/194 |
| 5,417,227 | A * | 5/1995 | West .......................... | A24F 1/00 131/185 |

(Continued)

FOREIGN PATENT DOCUMENTS

| | | | | |
|---|---|---|---|---|
| DE | 20001012 U1 * | 4/2000 | ............... | A24F 1/32 |
| GB | 820236 A * | 9/1959 | ............. | D21H 17/18 |

OTHER PUBLICATIONS

Rhein, "DE 20001012, machine translation", published Apr. 20, 2000.*

*Primary Examiner* — Alex Efta

(74) *Attorney, Agent, or Firm* — Tim Tingkang Xia, Esq.; Locke Lord LLP

(57) ABSTRACT

An electronic cigar is provided. The electronic cigar includes an inhalation portion and a body portion connected with the inhalation portion; a junction is formed by the connection between the inhalation portion and the body portion; the electronic cigar has an outer layer covering the junction and the junction edge adjacent areas. The electronic cigar looks beautiful, and the inhalation part and the body portion are securely connected.

6 Claims, 2 Drawing Sheets

(56) References Cited

U.S. PATENT DOCUMENTS

| | | | | |
|---|---|---|---|---|
| 2011/0277764 A1* | 11/2011 | Terry | ............... | A24F 47/008 |
| | | | | 128/203.26 |
| 2012/0261286 A1* | 10/2012 | Holloway | .......... | B65D 85/1054 |
| | | | | 206/268 |
| 2013/0061861 A1* | 3/2013 | Hearn | ............... | A24F 47/006 |
| | | | | 131/329 |
| 2013/0087160 A1* | 4/2013 | Gherghe | ............ | A24F 47/008 |
| | | | | 131/329 |
| 2013/0180533 A1* | 7/2013 | Kim | ............... | A24F 47/008 |
| | | | | 131/273 |
| 2013/0192622 A1* | 8/2013 | Tucker | ............... | H01C 17/00 |
| | | | | 131/329 |
| 2013/0255702 A1* | 10/2013 | Griffith, Jr. | .......... | A24F 47/008 |
| | | | | 131/328 |
| 2013/0306692 A1* | 11/2013 | Mangum | ............ | A24F 47/00 |
| | | | | 224/257 |
| 2014/0116455 A1* | 5/2014 | Youn | ............... | A24F 47/008 |
| | | | | 131/329 |
| 2014/0334804 A1* | 11/2014 | Choi | ............... | A61M 15/06 |
| | | | | 392/404 |

* cited by examiner

ELECTRONIC CIGAR

CROSS-REFERENCE TO RELATED APPLICATIONS

This application is a continuation of International Patent Application No. PCT/CN2013/076608, with an international filing date of May 31, 2013, designating the United States, now pending. The contents of these specifications are incorporated herein by reference.

BACKGROUND

Technical Field to Which the Invention Belongs

The present invention relates to an electronic cigar.

Related Art

At present, an electronic cigar usually has a connecting seam between the inhalation portion and the body portion, the connecting seam has not only made the appearance is not beautiful, but because the body portion and the inhalation portion can be disassembled, it will easily opened under the action of an external force.

It is an object to the invention to provide an electronic cigar which provides beautiful appearance and securely connection between the inhalation portion and the body portion.

SUMMARY

The above and other objects are achieved by the invention as described below.

An electronic cigar according to the invention comprises an inhalation portion and a body portion connected with the inhalation portion; a junction is formed by the connection between the inhalation portion and the body portion; the electronic cigar has an outer layer covering the junction and the junction edge adjacent areas.

The outside surface of the outer layer has a convex-shaped pattern and/or text.

The two ends of the outer layer are docked, and the outer layer covers the junction and the junction edge adjacent areas A concave area on the inhalation portion and the body portion is arranged and is corresponding to the area for placing the outer layer.

The shape of the concave area is adapted to the shape of the outer layer, the depth of the concave area is as same as the thickness of the outer layer, and the outer layer is embedded in the concave area.

The outside surface of the outer layer is coated with a non-slip layer.

The outside surface of the outer layer is covered with a transparent protective layer, and the outside surface of the transparent protective layer is coated with a non-slip layer.

The transparent protective layer is embedded in the concave area, and the total thickness of the outer layer and the transparent protective layer is equal to the depth of the concave area.

The length of the outer layer covering the inhalation portion and the length of the outer layer covering the body portion are respectively 2 mm~15 mm.

The connection between the inhalation portion and the body portion is detachable.

The inhalation portion and the body portion are connected together by way of threaded, buckle, magnetic, or interference fit.

The outer layer is made of tipping paper, copperplate paper, plastic paper or synthetic paper.

The inhalation portion only includes a suction nozzle, and the body portion includes an atomizing assembly and a power supply for providing power to the atomizing assembly.

The inhalation portion includes a suction nozzle and an atomizing assembly, and the body portion includes a power supply for providing power to the atomizing assembly.

In the electronic cigar according to the invention, an outer layer is configured and covers the junction and the junction edge adjacent areas, thus the electronic cigar looks beautiful, and the inhalation part and the body portion are securely connected.

DETAILED DESCRIPTION

An electronic cigar according to the invention will now be described in detail base on a preferred embodiment shown in the accompanying drawings.

Figure 1:
FIG. 1 is an overall configuration diagram of an embodiment of an electronic cigar according to the invention.
Figure 2:
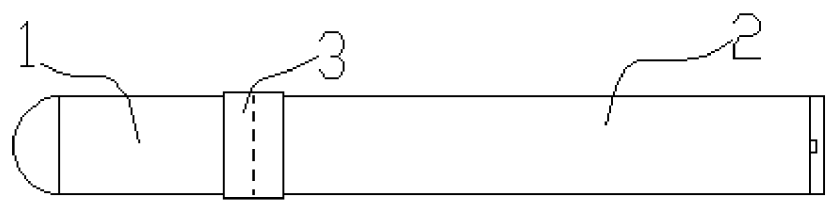
FIG. 2 is an overall configuration diagram of another embodiment of an electronic cigar according to the invention.

As shown in FIGS. 1 and 2, an electronic cigar according to the invention comprises an inhalation portion 1 and a body portion 2 connected with the inhalation portion 1; a junction 4 is formed by the connection between the inhalation portion 1 and the body portion 2; the electronic cigar has an outer layer 3 covering the junction 4 and the junction edge adjacent areas.

The inhalation portion 1 can only includes a suction nozzle, also can includes the suction nozzle and an atomizing assembly. If the inhalation portion only includes the suction nozzle, the body portion 2 includes the atomizing assembly and a power supply for providing power to the atomizing assembly; if the inhalation portion 1 includes both the suction nozzle and the atomizing assembly, the body portion 2 only includes the power supply for providing power to the atomizing assembly, at this situation the axial length of the inhalation portion 1 is longer and the atomizing assembly is located inside the inhalation portion 1.

The outside surface of the outer layer 3 can be printed with a convex-shaped pattern, and/or text, of course, can also be printed with a flat pattern and/or text, the outer layer 3 may be made of tipping paper, copperplate paper, plastic paper or synthetic paper. In the invention, a plastic paper is used to make the outer layer 3. Specifically, the outer layer 3 can be stickers, logo, etc.

Since the outer layer 3 is used, the connection between the inhalation portion 1 and the body portion 2 becomes more securely.

The two ends of the outer layer 3 are docked, and the outer layer 3 covers the junction 4 and the junction edge adjacent areas. Since the two ends of the outer layer 3 are docked, the outer layer 3 can easily be detached and changed. The covering can be achieved by pasting or buckling way.

Optionally, a double-sided adhesive or glue is provided between the outer layer 3 and the inhalation portion 1 and the body portion 2.

Such that the electronic cigar in a humid environment or water environment is not easy to fall off from the hands, the outside surface of the outer layer 3 is also coated with a non-slip layer.

The outer layer 3 can directly covers the outer surface of the electronic cigar (shown in FIG. 2, the outer layer 3 projecting from the outer surface of the electronic cigar).

Figure 3:
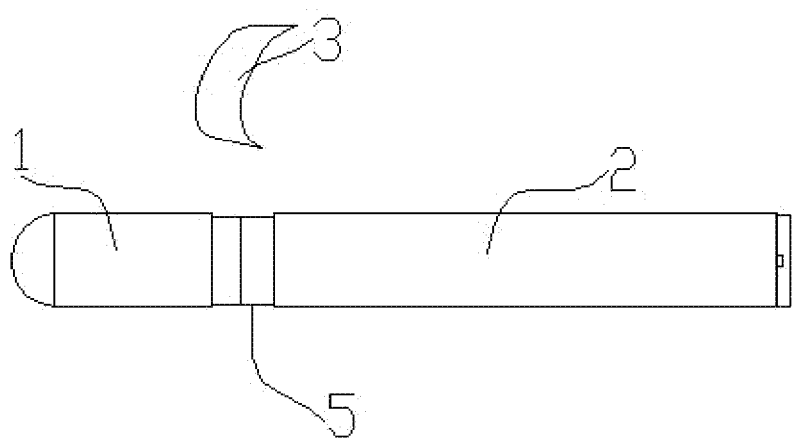
FIG. 3 is an exploded diagram of an electronic cigar and an outer layer according to the invention.

As shown in FIG. 3, A concave area 5 on the inhalation portion and the body portion is arranged and is corresponding to the area for placing the outer layer 3. The shape of the concave area 5 is adapted to the shape of the outer layer 3, the depth of the concave area 5 is as same as the thickness of the outer layer 3, and the outer layer 3 is embedded in the concave area; Thus the electronic cigar appearance is neat and beautiful.

Figure 4:
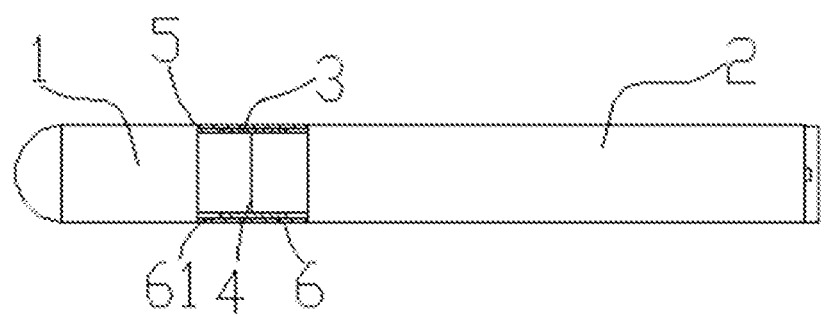
FIG. 4 is a configuration diagram of an electronic cigar having a protective layer according to the invention.

As shown in FIG. 4, the outside surface of the outer layer 3 can be covered with a transparent protective layer 6, and the outside surface of the transparent protective layer 6 is coated with a non-slip layer.

When the transparent protective layer 6 is used, the total thickness of the outer layer 3 and the transparent protective layer 6 is not limited, the total thickness can be equal to the depth of the concave area 5, so the whole outside surface of the electronic cigar is neat and beautiful, also as shown in FIG. 2, the transparent protective layer 6 projects from the outside surface of the electronic cigar.

In the above embodiment, the transparent protective layer 6 is a layer of plastics, silicone rubber the plastic layer. When the transparent protective layer 6 is elastic, it can be made as a sleeve and is fitted in the concave area 5 which is a ring groove. Or directly paste the transparent protective layer 6 on the concave area 5 and the outer layer 3. Preferably, the axial length of the transparent protective layer 6 is greater than or equal to the axial length of the outer layers 3.

The two ends of the transparent protective layer 6 can also be docked, so that the transparent protective layer 6 is easy disassembly, further the outer layer 3 is easy disassembly.

The transparent protective layer 6 can also be clamped in the outer of inhalation portion 1 and the body portion 2, in this situation, the axial length of the transparent protective layer 6 is greater than the axial length of the outer layers 3, so two axial edge areas 61 of the transparent protective layer 6 is beyond the outer layer 3. The inner sides of the two axial edge areas 61 are separately provided with a convex part or concave part, the inhalation portion 1 and the body portion 2 are separately provided with a concave part or convex part and the two convex parts or concave parts of the inner sides of the two axial edge areas 61 are arranged in the two concave parts or convex parts of the inhalation portion 1 and the body portion 2 (Not Shown in FIGS).

The transparent protective layer 6 arranged outside the outer layers 3 can prevent the outer layer 3 from being scratched or tear, by setting the anti-skid layer outside the outer layer 3, to prevent the electronic cigar from easily sliding from hands in the humid environment or other water environment.

In the embodiment above, two length ranges that the outer layer 3 is respectively sleeved on the inhalation portion 1 and the body portion 2 are all from 2 mm to 15 mm. Two length ranges of two axial edge areas 61 of the transparent protective layer 6 are from 2 mm to 10 mm. According to the invention, the two lengths that the outer layer 3 is respectively sleeved on the inhalation portion 1 and the body portion 2 are all 10 mm, two lengths of two axial edge areas 61 of the transparent protective layer 6 are 5 mm, for ensuring the appearance also having inhalation portion 1 and the body portion 2 connected firmly.

The inhalation portion 1 and the body portion 2 can be formed into one or detachably connected. When they are detachably connected, they are connected by way of screw thread, interference fit, buckle, magnet, wedge action or other means.

When connected by the way of screw thread, the inhalation portion 1 is provided with an inner screw thread, the body portion 2 is provided with external threads; or the inhalation portion 1 is provided with external threads, the body portion 2 is provided with internal thread.

When connected by the way of interference fit, the inhalation portion 1 in the mode of interference fit is inserted into or sheathed outside the body portion 2.

The electronic cigar is provided with the outer layer 3 which covers the junction 4 and the junction 4 edge adjacent areas of the inhalation portion 1 and the body portion 2. Thus, the electronic cigar looks beautiful, and the inhalation portion and the body portion are securely connected.

While the invention has been described based on the illustrated embodiments, the invention is not limited to them, and the configuration of each part may be replaced with any other configuration having same function, The invention may also be configured with other constituents.

What is claimed is:

1. An electronic cigar comprising: an inhalation portion; a body portion connected with the inhalation portion; and a junction formed by a connection between the inhalation portion and the body portion; wherein the connection between the inhalation portion and the body portion is detachable;
the electronic cigar further comprises an outer layer; two ends of the outer layer are docked and abut against the inhalation portion and the body portion respectively, and the outer layer covers the junction and junction edge adjacent areas by buckling;
wherein a concave area is arranged on the inhalation portion and the body portion and corresponds to the area for placing the outer layer;
wherein the concave area is a ring groove; the concave area is defined not only at one end of the inhalation portion but also at one end of the body portion; an inner peripheral surface of the outer layer is coated on outer peripheral surface of the concave area;
wherein a length of the outer layer covering the inhalation portion and a length of the outer layer covering the body portion are respectively from 2 mm to 15 mm;
wherein an outside surface of the outer layer is covered with a transparent protective layer which is a layer of plastic or silicone rubber, is made as an elastic sleeve and is fitted in the concave area, and a total thickness of the outer layer and the transparent protective layer is equal to the depth of the concave area; a shape of the concave area only allows a shape of the outer layer and the transparent protective layer to fit in; and
wherein the outer layer is made of tipping paper, copperplate paper, plastic paper or synthetic paper.

2. The electronic cigar according to claim 1, wherein an outside surface of the outer layer has a convex-shaped pattern and/or text.

3. The electronic cigar according to claim 1,
wherein, the axial length of the transparent protective layer is greater than the axial length of the outer layer; two axial edge areas are defined at two sides of the transparent protective layer along an axial direction; the length of the two axial edge areas ranges from 2 mm to 10 mm; inner sides of the two axial edge areas are separately provided with a convex part, the inhalation portion and the body portion are separately provided with a corresponding concave part and the two convex parts of the inner sides of the two axial edge areas are arranged in the two concave parts of the inhalation portion and the body portion.

4. The electronic cigar according to claim 1, wherein the inhalation portion and the body portion are connected together by a way of threaded, buckle, magnetic, or interference fit.

5. The electronic cigar according to claim 1, wherein the inhalation portion only includes a suction nozzle, and the body portion includes an atomizing assembly and a power supply for providing power to the atomizing assembly.

6. The electronic cigar according to claim 1, wherein the inhalation portion includes a suction nozzle and an atomizing assembly, and the body portion includes a power supply for providing power to the atomizing assembly.

* * * * *